(12) United States Patent
Brock et al.

(10) Patent No.: US 8,540,657 B1
(45) Date of Patent: Sep. 24, 2013

(54) METHOD AND APPARATUS FOR EQUINE PLASMAPHERESIS (75) Inventors: Kenny V. Brock, Notasulga, AL (US); Sara Ziska, Opelika, AL (US)

(73) Assignee: Auburn University, Auburn, AL (US)

( * ) Notice: Subject to any disclaimer, the term of this patent is extended or adjusted under 35 U.S.C. 154(b) by 867 days.

(21) Appl. No.: 12/614,298

(22) Filed: Nov. 6, 2009

Related U.S. Application Data

(60) Provisional application No. 61/198,673, filed on Nov. 7, 2008.

(51) Int. Cl.
*A61M 37/00* (2006.01)

(52) U.S. Cl.
USPC ............................ 604/6.06; 210/645; 210/782

(58) Field of Classification Search
USPC .............. 604/6.01, 6.04, 6.06; 210/645, 646, 210/782
See application file for complete search history.

(56) References Cited

PUBLICATIONS

Feige, K. et al, The effects of automated plasmapheresis on clinical, haemotological, biological and coagulation variables in horses. Veterinary J. 169, pp. 102-107. (2005).*
Simon, T, M.D. et al, Storage and transfusion of platelets collected by an automated two-stage apheresis procedure. Transfusion. 32:7, pp. 624-628. (1992).*

* cited by examiner

*Primary Examiner* — Melanie Hand
(74) *Attorney, Agent, or Firm* — Haverstock & Owens LLP (57) ABSTRACT

Methods of and apparatuses for equine plasma collection are provided. Modified plasmapheresis instruments and modified disposable plasmapheresis tubing are introduced. By using the modified procedures and instruments, a high-speed, high volume, continuous-flow process of automated equine plasmapheresis is developed. The modified closed systems remove whole blood from the donor horses, separate plasma from the cellular components of blood, and simultaneously returning concentrated cells back to the donor horses.

12 Claims, 6 Drawing Sheets

METHOD AND APPARATUS FOR EQUINE PLASMAPHERESIS

CROSS-REFERENCE TO RELATED APPLICATIONS

This application claims priority from U.S. Provisional Patent Application Ser. No. 61/198,673, filed Nov. 7, 2008 and entitled Method and apparatus for equine plasmapheresis, which is hereby incorporated herein by reference in its entirety for all purposes.

U.S. GOVERNMENT AGENCY AND THE GOVERNMENT CONTRACT

The invention was made by an agency of the United State Government or under a contract with an agency of the United State Government. The name of the U.S. Government agency and the Government contract number are: DHHS-PHS-Center for Disease Control Contract #200-2003-02695.

FIELD OF THE INVENTION

The present invention relates to the field of animal plasmapheresis processes and apparatus. More specifically, the present invention relates to the field of animal plasma collections.

BACKGROUND OF THE INVENTION

Plasmapheresis apparatus and procedures are often developed for the purpose of therapeutic therapies and plasma collections. In the plasmapheresis process, blood is removed from the body through needles or implanted catheters. The blood received is then sent through a cell separator to separate the plasma from other blood cells. In the therapeutic procedure, the blood cells are returned to the person under treatment. The plasma containing antibodies collected is either treated and then returned back to the patient or replaced with replacement plasma, albumin, or saline with added proteins. The plasmapheresis therapeutic procedure can be an effective treatment for autoimmune-disorders and other diseases, including Guillain-Barre syndrome, chronic inflammatory demyelinating polyneuropathy, Goodpasture's syndrome, hyperviscosity syndromes, and myasthenia gravis.

The plasma is able to be collected and stored for other uses. The plasma collected solely for the purpose of further manufacturing is called Source Plasma. Generally, the donors of the plasma need to go through a health check to ensure the safety of the plasma collected and the health of the donors. Two methods are often used for the plasma collection, including a manual method and an automated method. The manual method first collects blood from the donors. Next, the collected blood is separated by centrifuge machines in separate rooms. The plasma separated from the blood cells is gathered in a separate container. The red blood is returned back to the donor. The danger of this method is that there is a likelihood of returning red blood cells back to the wrong donor, which can cause a serious transfusion reaction. The automated method is similar to the manual method, but the difference is that the automated method performs all steps in a machine. As such, the chances of receiving the wrong red blood cells are eliminated.

Although plasmapheresis procedures and apparatuses have been used with human bodies, no plasmapheresis apparatus or method is specifically designed to be used with non-human being animals.

SUMMARY OF THE INVENTION

The methods of and apparatus for the equine plasmapheresis disclosed herein has been tested and experienced in conjunction with the Auburn University's Equine Source Plasma Project (AUESPP). The AUESPP was partly established for harvesting equine source plasma. The AUESPP has developed a high-speed, high volume, continuous-flow process of automated equine plasmapheresis. The designed closed system removes whole blood from donor horses, separates plasma from the cellular components of blood and simultaneously returns concentrated cells back to the donor horses. In some embodiments, the procedure is accomplished through adaptations made to human model Baxter A-200 Autopheresis-C instruments and through sterile modifications made to 4R-2252 Plasmacell-C disposable sets.

In one aspect, the present application is directed to a method of non-human plasma collection. The method of non-human plasma collection comprises receiving non-human blood from a donor animal, separating the non-human plasma from the non-human blood cells and returning the non-human blood cells back to the donor animal, and concurrently collecting the non-human plasma. The non-human blood contains non-human plasma and non-human blood cells.

In some embodiments, the method further comprises splitting the non-human blood received from the donor animal into a first portion and a second portion. In some embodiments, a first portion of the non-human blood is received at a first plasmapheresis device and a second portion of the non-human blood is received at a second plasmapheresis device. In some embodiments, the method further comprises adding an anticoagulation substance via an anticoagulation substance supplier to prevent coagulation of the blood in both the first and second plasmapheresis devices. In alternative embodiments, separating the non-human plasma from the non-human blood cells is via a non-human plasma separator in both the first and the second plasmapheresis devices. In other embodiments, the method of non-human plasma collection comprises a continuous-flow operation. In some embodiments, returning the separated non-human blood cells back to the donor animal occurs concurrently while a second non-human blood sample is received from the donor animal. In some embodiments, the method further comprises cooling the collected non-human plasma at a temperature below −10 degrees Celsius.

In an alternative aspect, the present application is directed to a system for collecting non-human plasma. The system for collecting non-human plasma comprises at least two non-human blood receiving devices and at least two non-human plasma separators coupled with the at least two non-human blood receiving devices. In some embodiments, the non-human plasma separators couple with a plasma collecting line and a blood returning line. In some embodiments, the plasma collecting line receives non-human plasma while the blood returning line simultaneously returns blood cells back to the donor animal.

In some embodiments, the system further comprises a donor blood line. In some embodiments, the donor blood line receives blood from a donor animal. In alternative embodiments, a tourniquet is wrapped around the neck of the donor animal, partially occluding an extraction vein but not obstructing the return vein, in order to provide adequate blood flow during a plasmapheresis procedure. In alternative embodiments, the donor blood line connects to a splitter. In some embodiments, the splitter splits the blood received from the donor animal into a first portion and a second portion. In other embodiments, the first portion of the blood received is transferred to the first non-human blood receiving device and the second portion of the blood received is transferred to a second non-human blood receiving device. In some embodiments, both the first and second non-human blood receiving devices contain an anticoagulation substance supplier for supplying an anticoagulation substance to prevent coagulation of the blood. In alternative embodiments, the non-human plasma separators separate the non-human plasma from the non-human blood cells. In other embodiments, the separated non-human plasma from both the first non-human plasma separator and the second non-human plasma separator are combined and collected as one unit. In other embodiments, the separated non-human blood cells from the first non-human plasma separator are combined with the separated non-human blood cells from the second non-human plasma separator and returned to the donor animal through one catheter.

In another aspect, the present application is directed to a method of modifying a plasmapheresis device. The method of modifying a plasmapheresis device comprises lengthening transmembrance lines to accommodate elevated transmembrane pressures associated with non-human plasmapheresis, combining tubing lines from two plasmacell-C disposable sets to allow dual instrument operation, having separated non-human blood cells bypass a device reservoir and instead return to the donor, modifying the sets to allow for the simultaneous processes of both collection and reinfusion, and sealing saline tubing lines.

In an alternative aspect, the present application is directed to a method of forming an animal plasma bank. The method of forming an animal plasma bank comprises maintaining a herd of animals, selecting donor animals from the herd of animals, receiving a first amount of blood from a first donor animal, isolating and collecting plasma contained in the first amount of blood, and returning the blood cells back to the donor animals concurrently and continuously when receiving a second amount of blood. In some embodiments, the blood comprises blood cells and plasma.

In some embodiments, the method further comprises collecting plasma from a second donor animal from the herd of animals. In alternative embodiments, the method further comprises collecting more than 20 liters of non-human plasma within 6 hours from the herd of animals. In other embodiments, the method further comprises splitting the first amount of blood received into at least two portions, wherein a first portion is directed to a first non-human blood separator on a first plasmapheresis instrument and a second portion is directed to a second non-human blood separator on a second plasmapheresis instrument. In alternative embodiments, the first portion and the second portion of the blood are substantially free of plasma and are combined into one portion before returning back to the donor animal. In other embodiments, the method further comprises cooling the collected plasma at a temperature below −10 degrees Celsius. In alternative embodiments, selecting donor animals comprises eliminating an animal as a donor animal when the animal has undergone a plasmapheresis procedure within 14 days.

DETAILED DESCRIPTION OF THE PREFERRED EMBODIMENT

The AUESPP operates on approximately 175 acres of secure pasture land located in north Auburn, Ala. Over thirty individuals are employed as full or part-time project members under the supervision of project director, Dr. Kenny Brock. Project employees include an international team of veterinarians, a quality control department, technical scientists, a project pharmacist, laboratory professionals and a crew of skilled farmhands. Maintained on the property is the project's impressive herd of nearly 200 draft horses. These horses are fundamental to the project's existence and continued success.

The AUESPP was established in October 2003 with the objective of harvesting equine source plasma. The AUESPP was established partly for harvesting equine source plasma. The AUESPP has developed a high-speed, high volume, continuous-flow process of automated equine plasmapheresis. The designed closed system removes whole blood from donor horses, separates plasma from the cellular components of blood and simultaneously returns concentrated cells back to the donor horses. The procedure is accomplished through adaptations made to human model Baxter A-200 Autopheresis-C instruments and through sterile modifications made to 4R-2252 Plasmacell-C disposable sets.

The AUESPP collects plasma from individual donor horses only after veterinary approval and a minimum fourteen day interval between plasmapheresis sessions. The designed method can safely harvest twenty liters of plasma from appropriate equine donors in less than six hours. Standard operating procedures (SOPs) have been developed detailing the collection method to ensure that each liter of equine plasma is collected following current good manufacturing practice (cGMP). After collection, the plasma is sterilely aliquoted into appropriately labeled 1 liter high density polyethylene bottles and frozen at −20 degrees Celsius. The plasma is stored in a locked, alarmed and continuously monitored freezer to ensure that the product remains at or below the −20 degrees Celsius standard. Designated lots of frozen plasma are packaged and shipped by the AUESPP upon request.

Procedures for the Equine Plasmapheresis Operation

The AUESPP operational procedure of the equine plasmapheresis is designed as a guide for conducting equine plasmapheresis. The procedure is able to be used in conjunction with Baxter's Operator's Manual for the Autopheresis-C Plasmapheresis System. The AUESPP operational procedures navigate through steps of the equine plasmapheresis procedure.

The AUESPP operational procedure includes descriptions of the modifications made to the Autopheresis-C instruments to allow for equine plasmapheresis, the modifications made to the Plasmacell-C sets to allow for equine plasmapheresis, and the procedures of performing equine plasmapheresis.

Descriptions of Model A-200 Autopheresis-C

Figure 1:
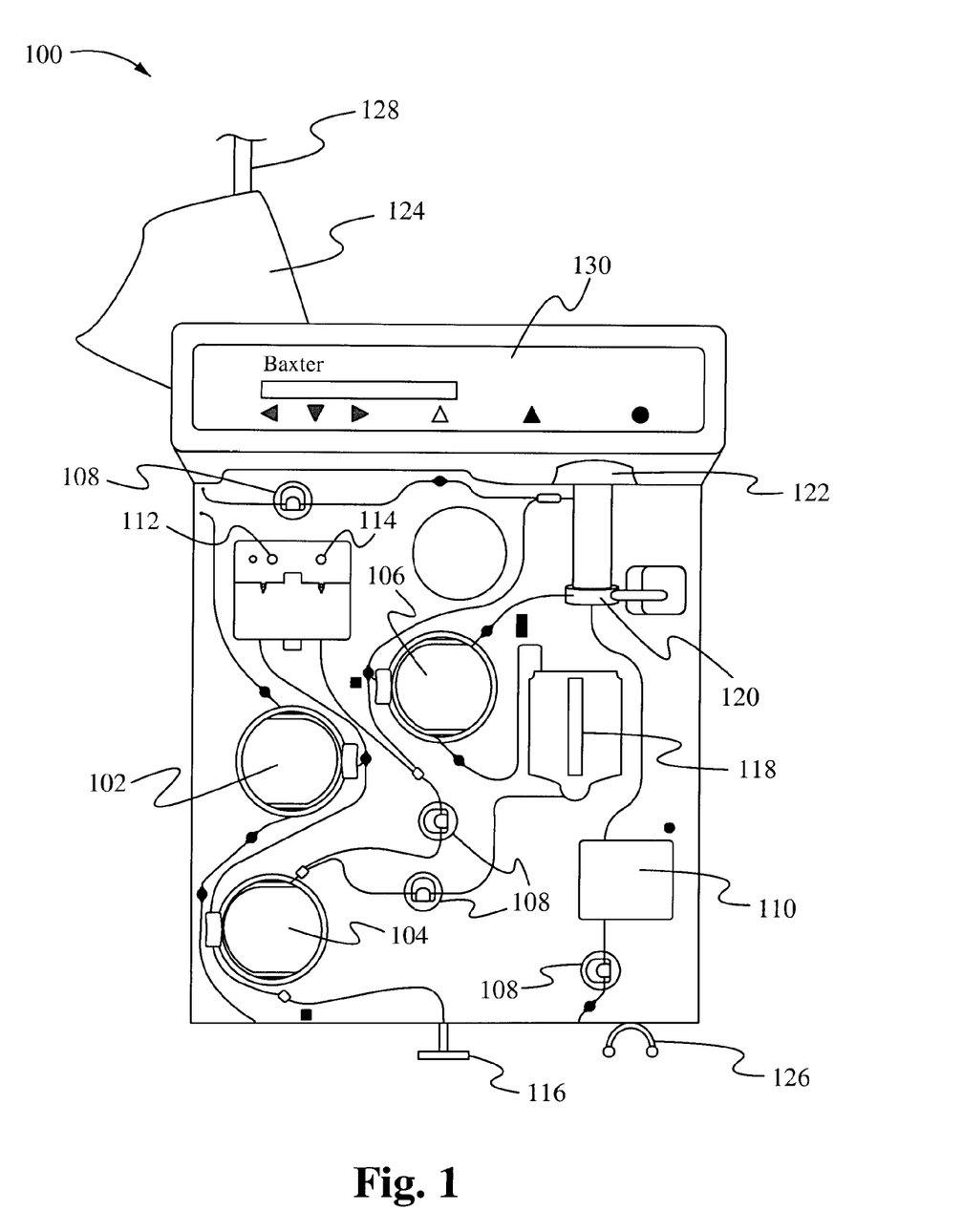
FIG. 1 illustrates the components of the Autopheresis system 100 for human use.

FIG. 1 illustrates the components of the currently available Baxter Model Autopheresis system 100 for human use. The Autopheresis system 100 includes an anticoagulant (AC)

pump 102, blood pump 104, cell pump 106, clamps 108, hemoglobin detector 110, venous pressure (P1) sensor 112, transmembrane pressure (P2) sensor 114, air detector 116, reservoir monitor system 118, device support 120, motor cup 122, pressure cuff 124, weigh scale 126, solution pole 128, and an operating panel 130. The Baxter Model Autopheresis is used as an examplary model in accordance with some embodiments of the present application. All the components of the Autopheresis system 100 are able to be modified for specific animal use in accordance with the embodiments of the present application. For example, the anticoagulant (AC) pump 102, the blood pump 104, the cell pump 106, the clamps 108, the hemoglobin detector 110, the venous pressure (P1) sensor 112, the transmembrane pressure (P2) sensor 114, the air detector 116, the reservoir monitor system 118, the device support 120, the motor cup 122, the pressure cuff 124, the weigh scale 126, the solution pole 128, and the operating panel 130 are all able to be specially designed for a particular animal or a type of animal use in accordance with the embodiments of the present application. Accordingly, the blood pump is able to be designed specifically for pumping horse blood. The horse blood pump is able to specifically pump horse blood only due to the different chemistry between horse and other animals, such as human beings. Similarly, the separator, described below, is able to be designed specifically for separating the equine plasma from other equine blood cells. The principle of designing a component that is specifically used for a particular animal is that different types of animals have different size of cells, different weight of individual or collective cells, different chemical contents of cells, or the combinations thereof. For example, the horse cell is able to be larger than the cell of human beings. Therefore, the components, in some embodiments, specifically designed for horse use are able to be applicable for human use and vice versa.

Modifications Made to Autopheresis-C for Equine Use

Figure 2:
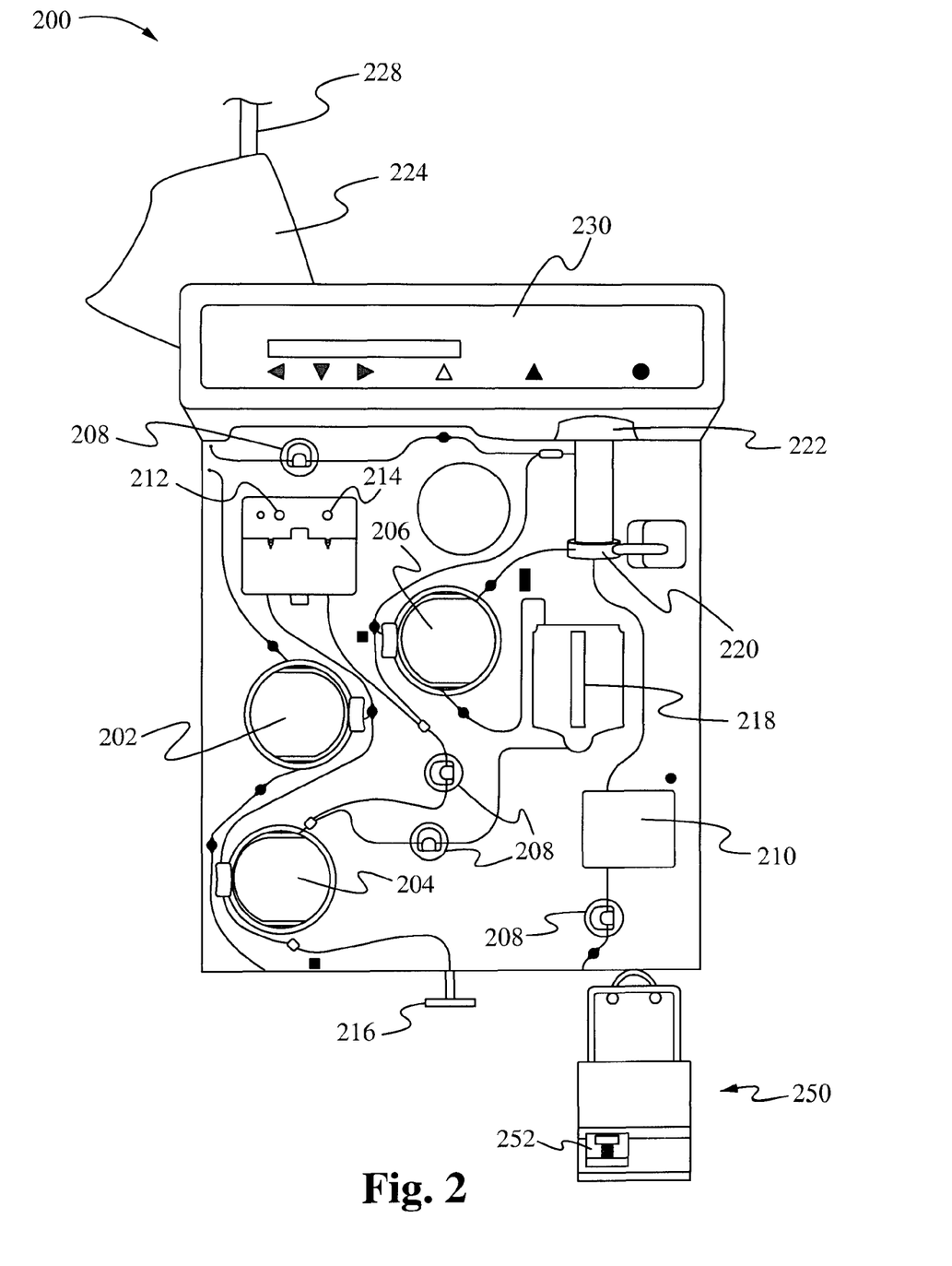
FIG. 2 illustrates an equine plasmapheresis system in accordance with some embodiments of the present application.

FIG. 2 illustrates the modifications made to the Model A-200 Autopheresis-C in accordance with some embodiments of the present application to allow the modified equine plasmapheresis instrument 200 to be used for equine plasmapheresis.

In some embodiments, the modified equine plasmapheresis instrument 200 includes an anticoagulant (AC) pump 202, blood pump 204, cell pump 206, clamps 208, hemoglobin detector 210, venous pressure (P1) sensor 212, transmembrane pressure (P2) sensor 214, air detector 216, reservoir monitor system 218, device support 220, motor cup 222, pressure cuff 224, external weight scale 250 (e.g. Ohaus Champ Square CQ50L Scale with CD33 indicator 252 weigh scale), solution pole 228, and an operating panel 230.

In some embodiments, the attached pressure cuff 224 is not used on the equine donor during plasmapheresis. Instead, the instrument's pressure cuff is able to be wrapped around a nearby portion of the stocks. In some embodiments, the cell pump 206 functions to immediately return blood cells to the donor and not to the reservoir.

Figure 5:
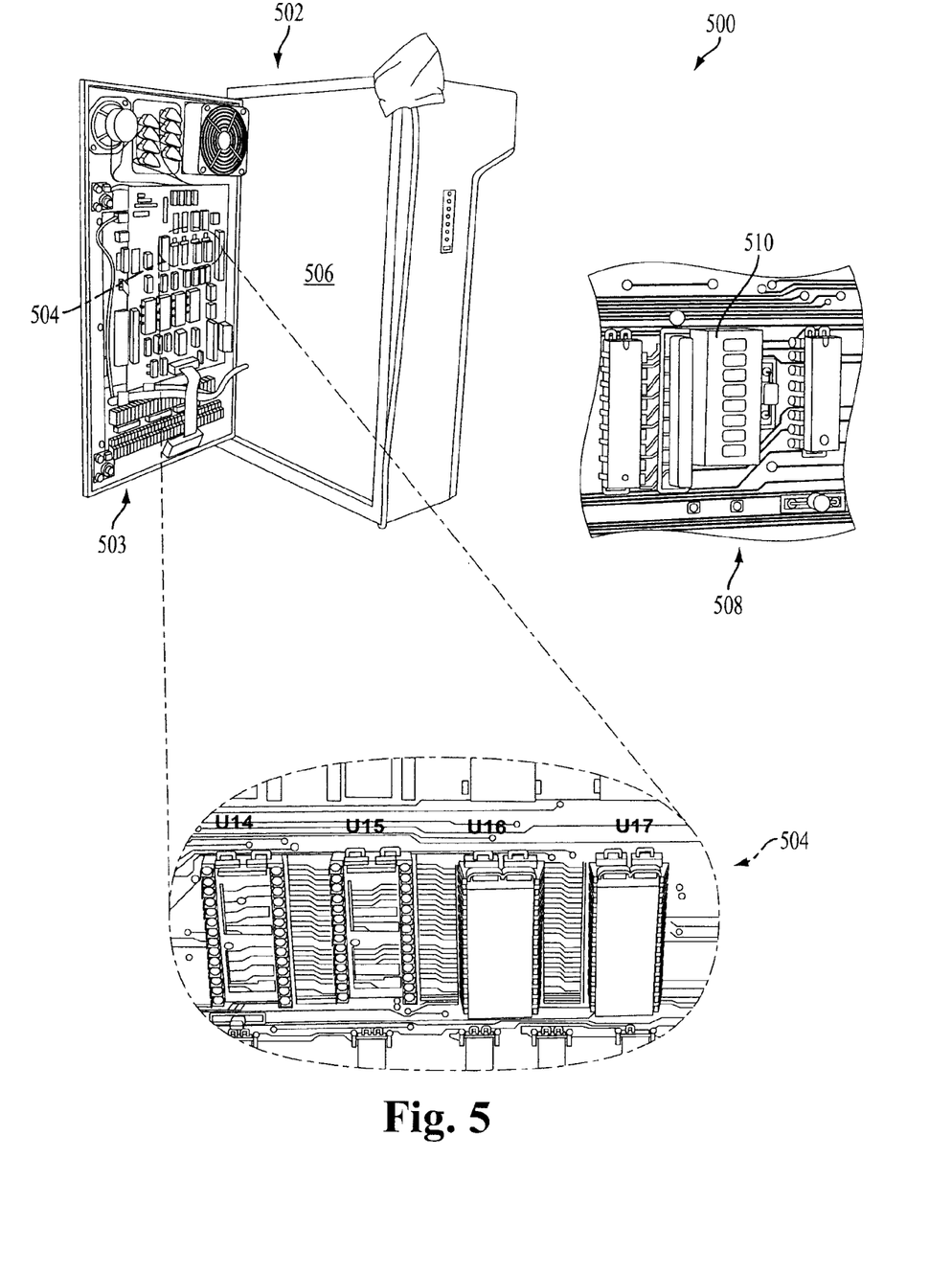
FIG. 5 shows a rear view of the internal console of the modified equine plasmapheresis system in accordance with some embodiments of the present application.

FIG. 5 shows a rear view of the internal console of the modified equine plasmapheresis system 500 in accordance with some embodiments of the present application.

The modified equine plasmapheresis system 500 contains the main body 502 of the equine plasmapheresis, which has the left panel 503 and the right panel 506. In some embodiments, the right panel 506 contains various pumps, sensors, tubing devices as described in FIG. 2 and associated descriptions. In some embodiments, the left panel 503 contains an electronic board having chip sets including a switch portion 508 and a chip set 504. In some embodiments, the switch portion 508 contains switch #8 of the DIP switch S1 510. In some embodiments, the switch #8 of the DIP switch S1 510 is permanently placed in the ON position. This prevents the "OK Blood Flow" message from being repeatedly displayed throughout the procedure.

Still referring to FIG. 5, in some embodiments, the chip set 504 contains chip ports U14, U15, U16, and U17. In some embodiments, the plasmapheresis at the AUESPP only requires the use of the chips U16 and U17 on the modified equine plasmapheresis 200 for instrument operation. In alternative embodiments, the chips U14 and U15 are removed from the CPU Board of the Autopheresis-C instruments. In some embodiments, Autopheresis-C version APA 2.0 Software for Veterinary Applications is installed on the modified equine plasmapheresis instruments 200.

Table 1 sets forth one set of configuration/default matrix settings in accordance with some embodiments of the present application. A no saline protocol is used for some embodiments of the present application.

TABLE 1

Configuration/Default Matrix for the equine plasmapheresis

| Menu Item/Display | Value |
|---|---|
| Change AC Ratio? NO | 6% |
| Change Plasma ml? NO | 1120 |
| Change Saline ml? NO | 50 |
| Change Parm View? NO | VIEW PARA NO |
| Change Adp Cuff? NO | 52 |
| Change Squeeze A? NO | 0 |
| Change Bld fib Rug? NO | High |
| Change Plas Max? | 1120 |
| Change P Grip? NO | NO |
| Change SAL/NO SAL? NO | PROTOCOL NO |
| Change Membrane? NO | Nylon |
| Change MAX DRAW? NO | 150 |
| Change MAX RETURN? NO | 130 |
| Change TMP SLOPE? NO | 39 |
| ChangeTMP Fudge? NO | 44 |
| Change spin 'b'? NO | 1500 |
| Change 'bHigh'? NO | 2200 |
| Change Spin 'c'? NO | 0 |
| Change Dyn Fdg? NO | 69 |
| Change ExtrFudge? NO | 44 |
| Change TMP Gain? NO | 0.75 |
| Change Damping? NO | 0.30 |
| Change Max up Vol? NO | 15 |
| Change Down Vol? NO | 16 |
| Change KickDown? NO | 96 |
| Change PQ PINK Fdg? NO | 0 |
| Change SPIN PINK D? NO | 0 R |
| Change LIPID PTL? NO | 32 |
| Change ESLOPECOOR? NO | 0.65 |
| Change HB RAT HALF? NO | 122 |
| Change Cuff? NO | 12 SEC |
| Change AC Size? NO | 500 |
| Reset Defaults? NO | NO |
| Begin APA 2.00 | |

Figure 3:
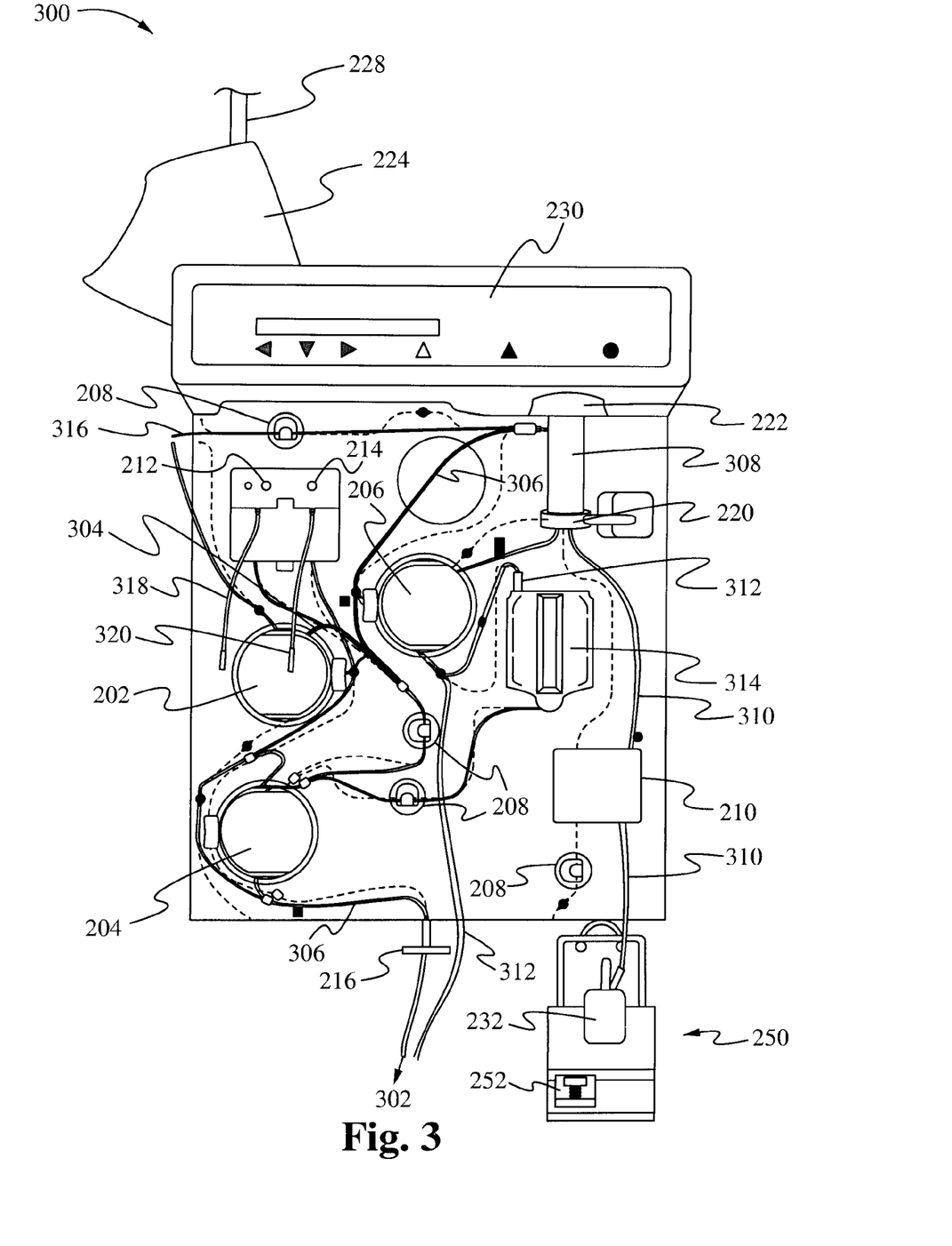
FIG. 3 illustrates an equine plasmapheresis system installed with modified Plasmacell-C Disposable set in accordance with some embodiments of the present application.

FIG. 3 illustrates an equine plasmapheresis system installed with modified Plasmacell-C disposable set in accordance with some embodiments of the present application. Now referring to FIG. 2 and FIG. 3. The anticoagulant (AC) pump 202 delivers sodium citrate solution at a controlled rate into a blood line 306. The blood pump 204 collects whole blood from donors and delivers anticoagulated blood to a separation device 308. The cell pump 206 receives concentrated cells from the separation device 308 and sends the concentrated cells through the cell line 312 back to the donor directly. The cell line 312 to reservoir 314 is sealed in some embodiments. The clamps 208 of the modified plasmapheresis instrument 200 open and close automatically during operation to control the flow of fluids traveling in the disposable set 300. The hemoglobin detector 210 is an optical sensor that monitors the plasma line for red blood cells and/or hemoglobin during operation. The venous pressure (P1) sensor 212 connects to the disposable set 300 and monitors the donor's venous pressure during operation. The transmembrane pressure (P2) sensor 214 connects to the disposable set 300 and monitors the transmembrane pressure within the separation device 308 during operation. The air detector 216 is an ultrasonic sensor that detects air in the blood line 306. The reservoir monitor system 218 contains four optical sensors for monitoring the fluid level in the reservoir—S1, RS1, S2, RS2. The device support 220 holds the separation device 308 in place during plasmapheresis. The motor cup 222 contains a magnetic cup that receives the separation device 308. In some embodiments, the pressure cuff 224 is able to be wrapped around the donor's vein and automatically inflates or deflates during operation. In some embodiments, the attached pressure cuff 224 is not used on the equine donor during plasmapheresis. Instead, the instrument's pressure cuff is able to be wrapped around a nearby portion of the stocks. In some embodiments, an external Ohaus Champ Square CQ50L scale 202 with CD33 indicator 204 is able to be used for weighing purposes during equine plasmapheresis.

Descriptions of Plasmacell-C Set

The modified Plasmacell-C set 300 illustrated in FIG. 3 is able to contain the following tubing lines, including the donor lines 302, anticoagulant lines 304, blood lines 306, separation device 308, plasma line 310, cell line 312, reservoir 314, saline line 316, venous (P1) line 318, and transmembrane (P2) line 320. The modified Plasmacell-C set 300 is able to be used with the modified equine plasmapheresis 200.

The donor line 302 receives whole blood from the donor and transports it to the modified equine plasmapheresis device 200. The anticoagulant lines 304 carries anticoagulant from its red spike, through the AC pump and delivers the sodium citrate to the whole blood at the Y shape connecter of the AC. The blood lines 306 carry anticoagulated whole blood past the air detector 216, through the blood pump 204 and to the separation device 308. The separation device 308 receives anticoagulated whole blood from the blood line 306. Plasma is separated from the cellular components of blood by a rotating membrane filter. The plasma exits the device and travels down the plasma line 310. The concentrated cells exit the device and are sent into the cell line 312. The plasma line 310 receives plasma from the separation device 308. The plasma line 310 passes through the hemoglobin detector 210 and delivers plasma to the collection container 232. The cell line 312 receives concentrated cells from the separation device 308, passes through the cell pump 206 and delivers the cells back to the animal donor directly. In some embodiments, the cells from the separation device 308 are able to be passed to the reservoir 314. In such case, the reservoir 314 receives and stores concentrated cells from the cell line. The saline line 316 begins at the saline Y and terminates in a clear spike. The venous (P1) line 318 connects to the venous pressure sensor 212 which monitors the donor's venous pressure during the process of plasmapheresis. The transmembrane (P2) line 320 connects to the transmembrane pressure sensor 214 which monitors transmembrane pressure in the separation device during plasmapheresis.

Custom Tubing Sets and Collection Bag Used in Modified Set Production

Charter Medical 03-220-EPS1 Tubing Set (EPS1)

In some embodiments, the sterile custom tubing set consists of two 36 inch long lines which join at a Y junction. A single 76 inch long line extends from the Y piece. The single line contains an infusion port and ends in a luer connection. During equine plasmapheresis, this tubing carries concentrated cells from the cell lines 312 of the modified disposable set 300 to the horse's return catheter.

Charter Medical 03-220-EPS2 Tubing Set (EPS2)

In some embodiments, the sterile custom tubing set consists of two 28 inch long lines which join at a Y junction. A single 36 inch long line with an infusion port extends from the Y piece. During equine plasmapheresis, this tubing carries plasma from the plasma lines 310 to the EPS-20L collection bag 232.

Charter Medical 03-220-EPS3 Tubing Set (EPS3)

In some embodiments, the sterile custom tubing set consists of two 36 inch long lines which join at a Y junction. A single 16 inch long line extends from the Y piece. The single line contains an infusion port and ends in a luer connection. During equine plasmapheresis, this tubing line attaches to the donor's extraction catheter and delivers whole blood to the modified disposable set 300. In some embodiments, the term modified disposable set 300 is interchangeable with the term modified plasmacell-C set.

Charter Medical EPS-20L Collection Bag (EPS-20L)

In some embodiments, the 20 liter capacity gamma irradiated EVA bag 232 is equipped with 3 ports. Two ports provide possible tubing connections, while the third port provides sterile sampling access. During equine plasmapheresis, plasma is delivered to the 20 liter bag 232 through the centrally located tubing port.

Materials for Modified Plasmacell-C Set Production

In some embodiments, the materials for the modified plasmacell-C set production include the supplies of two of the Baxter 4R-2252 Plasmacell-C Disposable Sets, Charter Medical EPS1 tubing set, Charter Medical EPS2 tubing set, Charter Medical EPS3 tubing set, Charter Medical EPS-20L bag, 36 inches of spare sterile tubing, 14 inch saline line sealing guide, Nalgene tub, bag liner, and lot number tracking card. In some embodiments, the equipment needed for modified plasmacell-C set production includes Terumo TSCD Sterile Tubing Welder and Baxter AutoSeal Tubing Sealer.

Protocol for Building the Modified Plasmacell-C Set

In some embodiments, the protocol for building the modified Plasmacell-C Set is able to include the following steps:

Both 4R-2252 sets are opened and placed on the work top surface. The sets are oriented to position the separation device upright with the plasma line exiting the bottom of the device. Next, the cell line of one 4R-2252 set is located. The Baxter AutoSeal Tubing Sealer is used to seal the cell line where it enters the reservoir. The procedure is repeated on the remaining 4R-2252 set. Next, the saline line of one 4R-2252 set is located. The saline line ends in a clear spike and is bundled with the P1 and P2 lines. The saline line is isolated and the line is sealed approximately 14 inches from the spiked end using a sealing guide or a ruler. The sealed line is separated and discarded. The procedure is repeated on the remaining 4R-2252 set. Next, the Charter Medical EPS3 tubing pack is open. The donor line of one 4R-2252 set is welded onto one 36 inch long line of the EPS3 tubing. The procedure is repeated with the remaining 4R-2252 set and the remaining 36 inch long line of the EPS3 tubing. The EPS3 line is bundled to prevent tangling.

Next, the Charter Medical EPS1 tubing pack is opened. The previously sealed cell line of one set is separated and is welded onto one 36-inch long line of the EPS1 tubing. The procedure is repeated with the remaining disposable set and the remaining 36 inch long line of the EPS1 tubing. The EPS1 line is bundled to prevent tangling. Next, the P2 line of one 4R-2252 disposable set is located. The P2 line is lengthened by welding approximately 18 inches of spare sterile tubing into the line. The connector is welded back onto the end of the lengthened P2 line. The procedure is repeated on the P2 line of the remaining set.

Following the completion of the above steps, the modified set is stored in a Nalgene tub. The bag liner and lot number tracking card are added to the tub. Lot numbers for EPS1, EPS3, and Plasmacell-C Set are identified on the tracking card. Charter Medical EPS2 tubing and Charter Medical EPS-20L bag are added to the Nalgene tub and identified on the Tracking Card prior to initial set installation. Charter Medical EPS2 tubing and Charter Medical EPS-20L bag are welded onto the modified disposable set during the "Install Set" portion of plasmapheresis. The welding procedure is described in detail later.

Summary for Modifying the Plasmacell-C Set

In some embodiments, the two separate 4R-2252 Plasmacell-C sets are welded together into one modified set for dual instrument operation. The saline lines are sealed reflecting the NO SALINE PROTOCOL adopted by the AUESPP. The P2 lines are lengthened on the modified set to accommodate the frequently encountered elevated transmembrane pressures associated with equine plasmapheresis. Finally, the sets are modified to allow for the simultaneous processes of both collection and re-infusion. During equine plasmapheresis, the Charter Medical EPS3 tubing line receives whole blood from the donor's extraction catheter. The EPS3 tubing carries whole blood to the donor lines of the modified set. Anticoagulant is added to the lines as the blood travels toward the two simultaneously operating modified equine plasmapheresis system 200. The term modified equine plasmapheresis system, instrument, or device 200 used in this disclosure is interchangeable with the term Autopheresis-C instruments. The anticoagulated whole blood travels through the blood lines 306 to each instrument's separation device 308. Concentrated cells exit each separation device 308 and enter the cell lines 312. During equine plasmapheresis, the concentrated cells bypass the reservoir 314 and are immediately returned to the horse or donor animal via the Charter Medical EPS1 tubing line. Plasma exits each separation device 308 and travels down the plasma lines 310. During equine plasmapheresis, the plasma lines 310 join the Charter Medical EPS2 tubing set which carries the plasma to the EPS-20L collection bag 232.

Preparation for Equine Plasmapheresis

Preparation for equine plasmapheresis at the AUESPP begins well in advance of the actual procedure. Specific preparatory tasks are carried out at different time intervals prior to an equine plasmapheresis session. The following is a detailed list of the tasks performed according to time.

Tasks Performed Greater than 24 Hours Prior to Plasmapheresis:

The steps of supply preparation include building modified Plasmacell-C sets for dual equine plasmapheresis instrument 200 operation, ensuring there is a sufficient number of modified Plasmacell-C sets for plasma collection, and ordering any necessary supplies from the Supplies Coordinator. Table 2 illustrates a supply inventory in accordance with some embodiments of the present application.

TABLE 2

| General Supplies: | |
| --- | --- |
| 4x4 gauze | 1 inch white porous tape |
| Alcohol prep pads | Boxes of exam gloves sizes XS-XL |
| 4 inch Elastikon | 4 inch VetFlex cohesive bandage material |

TABLE 2-continued

| | |
| --- | --- |
| Infusion plugs | 5 ml BD Vacutainer Plasma Preparation Tubes |
| Surgical drape material | BD Vacutainer Luer-Lok Access Devices |
| 2-0 Supramid sutures | 500 ml bags Baxter Anticoagulant Sodium Citrate Solution |
| #15 blades | 1 ml, 3 ml, & 30 ml syringes |
| Sandwich bags | 18 gauge & 20 gauge 1.5 inch needles |
| Adhesive/duct tape | 5 L bags Baxter Plasma-Lyte A |
| Boxes of Kemwipes | 72 inch large animal IV sets |
| Sharps containers | Spray bottle of 70% ethanol |
| Detomidine | 2% Lidocaine HCl |
| Butorphanol | Labels |
| | Scrub Cart Supplies: |
| Nolvasan Surgical Scrub | ChloraPrep One-Step applicators |
| 4x4 gauze | Boxes of exam gloves sizes XS-XL |

Tasks Performed 12-24 Hours Prior to Plasmapheresis:

In some embodiments, the collection room preparation is performed 12-24 hours prior to the process of plasmapheresis. The preparation includes the following steps:

(1) using adhesive to hang surgical drape material from the stocks;

(2) positioning two modified equine plasmapheresis instruments 200 adjacent to one another at the head of the stocks;

(3) wrapping the modified equine plasmapheresis instruments 200 blood pressure cuffs onto the stocks;

(4) plugging the modified equine plasmapheresis instrument 200 into the yellow power cords;

(5) positioning one Ohaus Champ Square CQ50L scale next to the modified equine plasmapheresis instrument 200;

(6) balancing the Ohaus Champ Square CQ50L scale;

(7) hanging two or three 500 ml bags of Baxter Anticoagulant Sodium Citrate Solution from the solution pole of each modified equine plasmapheresis instrument 200;

(8) placing the following materials on the top of the modified equine plasmapheresis instrument 200:
  (a) several alcohol prep pads,
  (b) one roll of 4 inch VetFlex cohesive bandage material,
  (c) several infusion plugs,
  (d) two 2-0 Supramid sutures,
  (e) two 3 inch pieces of white porous tapes,
  (f) one roll of 4 inch Elastikon in a protective sandwich baggie;

(9) performing initial installation of the modified Plasmacell-C sets;

(10) opening and placing the Charter Medical EPS2 tubing on top of the modified equine plasmapheresis instrument 200;

(11) opening the EPS-20L bag, slipping it into the bag liner and placing it in the Nalgene tub;

(12) placing the green Lot# Tracking Card on the work station cart;

(13) placing one sharps container on the collection room floor next to the modified equine plasmapheresis instrument 200;

(14) placing one tourniquet splint on the collection room floor next to the stocks;

(15) placing the following West Nile Virus sampling supplies on the work station cart:
  (a) two 5 ml BD Vacutainer plasma preparation tubes (if temperature permitting),
  (b) one BD Vacutainer Luer-Lok access device with 20 gauge 1.5 inch needle attached, and
  (c) one 3 ml syringe with 20 gauge 1.5 inch needle attached;

(16) placing appropriate forms on each work station cart;
(17) placing appropriate liners in medical waste and trash bins;
(18) preparing the silver scrub cart with the following materials:
 (a) boxes of exam gloves sizes XS-XL,
 (b) box of ChloraPrep One-Step,
 (c) canisters of 4×4 gauze applicators,
 (d) squeeze bottles of Nolvasan Surgical Scrub;
(19) drawing up sodium citrate solution into labeled 30 ml syringes and placing approximately 4-6 syringes on the modified equine plasmapheresis instrument 200; and
(20) drawing up Detomidine into labeled 1 ml syringes and place approximately 3-4 syringes per donor on the work station cart.

Tasks Performed Immediately Prior to Plasmapheresis:

In some embodiments, the tasks that are performed immediately prior to plasmapheresis include:
(1) turning on all collection room lights, exhaust fan and fly fan;
(2) plugging Ohaus Champ Square Scales into the yellow power cords;
(3) performing the quality control check of the Ohaus Scales and recording on the appropriate form; and
(4) obtaining the following items from the product room:
 (a) Terumo TSCD Sterile Tubing Welders,
 (b) Baxter AutoSeal Tubing Sealers, and
 (c) one cool pack per donor.

Procedure for Initial Installation of the Modified Plasmacell-C Set

The following procedure illustrates the initial installation of the modified Plasmacell-C set in accordance with some embodiments of the present application:
(1) obtaining from the product room a Nalgene tub containing a modified Plasmacell-C set, Charter Medical EPS2 tubing, Charter Medical EPS-20L bag, bag liner, and Lot# Tracking Card;
(2) placing the Nalgene tub and contents between the two adjacent modified equine plasmapheresis instrument 200, which remain OFF during this installation procedure in some embodiments of the present application;
(3) beginning disposable set installation on the modified equine plasmapheresis instrument 200 located nearest the head of the stocks;
(4) picking up one separation device 308 and the tubing components associated with that separation device;
(5) inserting the separation device 308 into the motor cup 222, raising the device support 220 upward, and clicking the separation device 308 into place;
(6) stretching the sealed saline line across the top of the instrument and behind the saline clamp;
(7) sliding the top of the reservoir 314 into the reservoir channel, pressing the bottom of the reservoir into the channel to lock into place, while the disposable set tubing is not pinned behind the reservoir;
(8) identifying the concentrated cell line 312 where it exits from the bottom of the separation device 308, placing the concentrated cell line 312 into the tubing guide at the top of the cell pump 206, rolling the tubing onto the cell pump 206 and into the tubing guide at the bottom of the pump, and closing the cell pump 206 by turning the handle;
(9) identifying the blood line 306 where it enters the separation device 308, positioning the blood line 306 around the cell pump 206, into the tubing guide, and behind the blood clamp 208;
(10) positioning the reinfusion line behind the reinfusion clamp 208;
(11) sliding the reservoir Y into the tubing guide above the blood pump 204;
(12) rolling the blood line 306 onto the blood pump 204, positioning the P1 Y against the tubing guide at the bottom of the blood pump, and closing the blood pump;
(13) flossing the blood line into the air detector 216 and spining the black wheel to a closed position;
(14) looping the venous pressure (P1) line 212 around the blood pump 204 and upward around the anticoagulant pump 202 and positioning the tubing into appropriate tubing guides;
(15) installing the P1 line 318 behind the left hand side of the pressure transducer cover and pulling the P1 line 318 into both cover slots;
(16) installing the transmembrane pressure (P2) line 320 behind the right hand side of the pressure transducer cover and pulling the P2 line 320 into both cover slots;
(17) allowing approximately six inches of P1 and P2 tubing extending from the top of the pressure transducer cover; whereas, the connectors to the sensors should not be attached and the cover should not be closed at this time;
(18) identifying the anticoagulant (AC) tubing line, looping the AC line onto the AC pump 202 and closing the pump door, positioning the red tube stops against the top and bottom tubing guides, and wrapping the remaining AC line and associated red spike around the solution support pole until needed;
(19) not manipulating the plasma line 310 at this time, and not inserting plasma line 310 into the hemoglobin detector 210 or placing behind the plasma clamp 208;
(20) repeating steps 4 through 19 with the remaining disposable set and the remaining modified equine plasmapheresis instrument 200;
(21) obtaining three blue plastic hemostats from the work station cart, placing one hemostat on the Charter Medical EPS1 tubing line between the Y piece and the infusion port, and placing the two remaining blue hemostats on each donor line before the AC Y; and
(22) resting the Charter Medical EPS1 and EPS3 tubing lines between the adjacent instruments and onto the stocks.

Above steps are described as examples, all steps are optional. Additional steps are able to be added. The sequences of the above steps are able to be performed in any order.

Veterinary Tasks Performed within 24 Hours of Plasmapheresis

The following procedure describes the veterinary tasks that need to be performed within 24 hours of plasmapheresis:
(1) identifying a donor horse from the plasmapheresis schedule;
(2) initiating appropriate paperwork for plasmapheresis;
(3) conducting a record review of the donor horse: if the result shows that the donor is on deferral and determined unsuitable for plasmapheresis, the plasmapheresis procedure for the donor is deferred; however, if the result shows that the donor is not on deferral and determined suitable for plasmapheresis, the next step is performed;
(4) bringing the suitable donor horse to the Treatment Barn and performing the following steps:
 a. verifying the horse's identification,
 b. performing physical examinations,
 c. clipping a large rectangle of hair from over each jugular vein,
 d. collecting EDTA (purple top) and serum (red top) blood tubes;

(5) determining the donor horse's total protein using a refractometer. The total protein must be greater than 5.5 g/dl.

Veterinary Tasks Performed Immediately Prior to Plasmapheresis

The following description describes veterinary tasks needed to be performed immediately prior to plasmapheresis. The steps included are:

(1) bringing the suitable donor horse to the Treatment Barn and verifying its identity;
(2) weighing the horse on the Equine Platform Scale;
(3) determining the horse's temperature using an NIST traceable rectal thermometer, and the temperature must be less than 103.0° F.;
(4) determining the status of the donor as:
   a. accepted for plasmapheresis,
   b. rejected for plasmapheresis, or
   c. temporarily deferred;
(5) sedating the accepted donor horse with Detomidine intravenously and leading into the collection room;
(6) securing the horse in the stocks with a rear rope and back rope, situating the horse's head in a padded sling, while resting its chest against the door of the stocks;
(7) preparing the clipped area over each jugular vein for catheterization using the supplies located on the silver scrub cart and performing the following steps along step 7 including:
   a. donning exam gloves and obtaining 4×4 gauze with a "clean" hand,
   b. transferring 4×4 gauze to "dirty" hand and squeezing Nolvasan Surgical Scrub onto gauze,
   c. scrubbing the entire clipped area with the gauze and Nolvasan Surgical Scrub,
   d. repeating the process until the gauze remains clean following the scrub,
   e. obtaining a ChloraPrep One-Step applicator with "clean" hand and releasing the antiseptic,
   f. rubbing the applicator over the jugular furrow with repeating strokes for 30 seconds,
   g. allowing 30 seconds for the area to dry; and
(8) performing catheterization by AUESPP veterinarians using the following method:
   a. injecting 2% Lidocaine HCl subcutaneously over each catheterization site,
   b. donning sterile gloves,
   c. producing a small skin incision in each anesthetized area using a #15 blade,
   d. placing a 10 gauge 3.00 inch BD Angiocath catheter directed ventrally into the horse's jugular vein,
   e. capping catheter with an infusion plug,
   f. placing a 10 gauge 3.00 inch BD Angiocath catheter directed ventrally into the remaining jugular vein,
   g. capping catheter with an infusion plug, and
   h. securing catheters into place with a suture.

Veterinary Supply Inventory

Table 3 illustrates the veterinary supply inventory in accordance with some of the embodiments of the present application.

TABLE 3

Veterinary Supply Inventory

BD Vacutainer EDTA blood tubes (purple tops)
BD Vacutainer Serum blood tubes (red tops)
20 guage 1.5 inch Vacutainer needles
Capillary tubes and Clay TABLE 3-continued Veterinary Supply Inventory Distilled water
1 ml & 3 ml syringes
18 gauge & 20 gauge 1.5 inch needles
15 blades
Exam and Sterile Gloves
10 gauge 3.00 inch BD Angiocath catheters
2-0 Supramid sutures
Infusion plugs
2% Lidocaine HCl
Detomidine
Butorphanol Performing Equine Plasmapheresis at the AUESPP I. Plasmapheresis: Instrument Start Up The side-by-side modified equine plasmapheresis instruments 200 are powered on and advanced simultaneously. The following steps are performed:

(1) turning on the modified equine plasmapheresis instruments 200 by flipping the power switch located on the back of the units;
(2) pressing ∇ to advance after seeing "Self Test" and "Turn OFF Sw 8" messages appearing on the display panel;
(3) pressing the STOP button located on the far right of the operating panel after the "Test (Press STOP)" is displayed and pressing ∇ to advance when "Plasmapheresis" is displayed;
(4) pressing ∇ to advance after seeing the software information and protocol settings scrolling across the display, which is followed by a showing of "NOT FOR HUMAN USE"; and
(5) allowing the modified equine plasmapheresis instruments 200 to verify the operating parameters during instrument calibration, and the information regarding authorized use of the unit will scroll across the display followed by the message of "Calibration," allowing the showing of "Install Set" on the display after the instrument passes calibration.

II. Plasmapheresis: Set Installation

Installation and modification of the dual Plasmacell-C set is completed during "Install Set." A Terumo welder is required for the procedure. In some embodiments, the following steps are performed:

(1) obtaining the EPS2 tubing assigned to the modified set, welding one 28 inch long line of the EPS2 to one plasma line, closing the plasma line behind the hemoglobin detector door, sliding the plasma line into the plasma clamp, attaching pressure sensors, closing the transducer cover on the associated instrument;
(2) welding the remaining 28 inch long line of the EPS2 to the remaining plasma line, closing the plasma line behind the hemoglobin detector door, sliding the plasma line into the plasma clamp, attaching pressure sensors, closing the transducer cover on the associated instrument;
(3) welding the 36 inch long line of the EPS2 to the centrally located tubing port on the designated EPS-20L bag, placing a cool pack on the bottom of the Nalgene tub and setting the 20L bag with its liner on top;
(4) placing the Nalgene tub and its contents onto the Ohaus Champ scale, taring the displayed weight;
(5) continuing with set installation by pressing the ∇ button, and "Check Reservoir" will be displayed, verifying that the reservoir is properly installed, and pressing ∇ to advance;

(6) verifying that blue hemostats are placed on each donor line and the EPS1 line when the display shows "CLAMP TUBING END," pressing ∇ to advance;

(7) allowing instruments to perform an installation check while "INSTALL CK" is displayed, advancing the modified equine plasmapheresis instruments 200 to "CONNECT AC" after a successful check.

III. Plasmapheresis: Anticoagulant Priming

In some embodiments, the entire EPS3 tubing set and both blood lines are primed with sodium citrate solution before the modified equine plasmapheresis instruments 200 is advanced to "Venipuncture." Both solution connection and set priming are performed wearing exam gloves. In some embodiments, the following steps are performed:

(1) donning exam gloves and aseptically spiking the sodium citrate bag of each instrument with the associated red AC line spike;

(2) grasping the EPS3 tubing set, moving both blue hemostats from the donor lines to the blood lines, removing the white cap from the luer end of the EPS3 line;

(3) performing the solution priming on each instrument individually, priming the tubing by pressing ∇ on one instrument, allowing the display of "AC Priming," allowing the AC pump delivering sodium citrate at the level of the donor line, allowing the sodium citrate to continue down the EPS3 tubing, moving the blue hemostat back to the donor line once the sodium citrate reaches the EPS3 Y, which allows the anticoagulant to prime the blood line, allowing the message "Turn off dip switch 8" to appear after the solution reaches the air detector, and the priming of this instrument is completed;

(4) pressing ∇ to initiate priming on the remaining instrument, priming sodium citrate past the EPS3 Y and to the tip of the EPS3 luer when priming the second instrument, moving the blue hemostat back to the donor line to allow priming of the blood line, allowing the message "Turn off dip switch 8" to appear after priming is complete, replacing the white cap on the end of the EPS3 tubing, (In some embodiments, both instruments require two priming cycles. An alarm will sound and "NO FLUID DETECTED" will appear after the first cycle.) pressing the Δ button to return to "Connect AC" display and pressing the ∇ button to repeat "AC Priming";

(5) advancing both instruments with the ∇ button, until the display shows "Percent AC=6%," continuing to press ∇ until "OPEN BLOOD PUMP" appears, opening the blood pumps to equalize pressure throughout the modified set, closing the blood pumps and press ∇;

(6) inflating the pressure cuffs to 36 mmHg by pressing the + button when "Venipuncture" is displayed.

IV. Plasmapheresis: Donor Verification and Connection

In some embodiments, the donor is verified with appropriate paperwork and the disposable set is connected to the donor before the instruments are advanced further. The following steps are performed at this stage:

(1) verifying the donor's primary and secondary identification along with the donor's approval for plasmapheresis;

(2) assigning the accepted donor a unique collection number and initiating appropriate plasmapheresis paperwork;

(3) labeling the unique collection number and affiliated bar code on the donors plasma preparation tubes and on the donors 20 liter collection bag, labeling the collection bag with the equine donor's primary identification, secondary identification, and the donor's weight;

(4) using the two labeled plasma preparation tubes for donor West Nile Virus testing, obtaining the blood samples using the following method:
  a) donning exam gloves,
  b) swabbing infusion plug of catheter with alcohol pad,
  c) removing trash blood from the jugular catheter using a 3 ml syringe,
  d) disposing of trash blood syringe in sharps container,
  e) using access device to fill both plasma tubes,
  f) inverting the tubes gently 8-10 times, and
  g) spinning the samples in the IEC Centra centrifuge and freezing at −20 degrees C.;

(5) attaching the EPS1 and EPS3 tubing lines to the donor's catheters via luer connections, routinely connecting the EPS3 to the near/right catheter, while EPS1 is connected to the far/left catheter, securing both tubing lines to the donor's neck with sutures;

(6) wrapping a tourniquet around the horse's neck to provide adequate blood flow for plasmapheresis. The tourniquet consists of a roll of Elastikon, a roll of VetFlex bandage material and a PVC splint.

Figure 6:
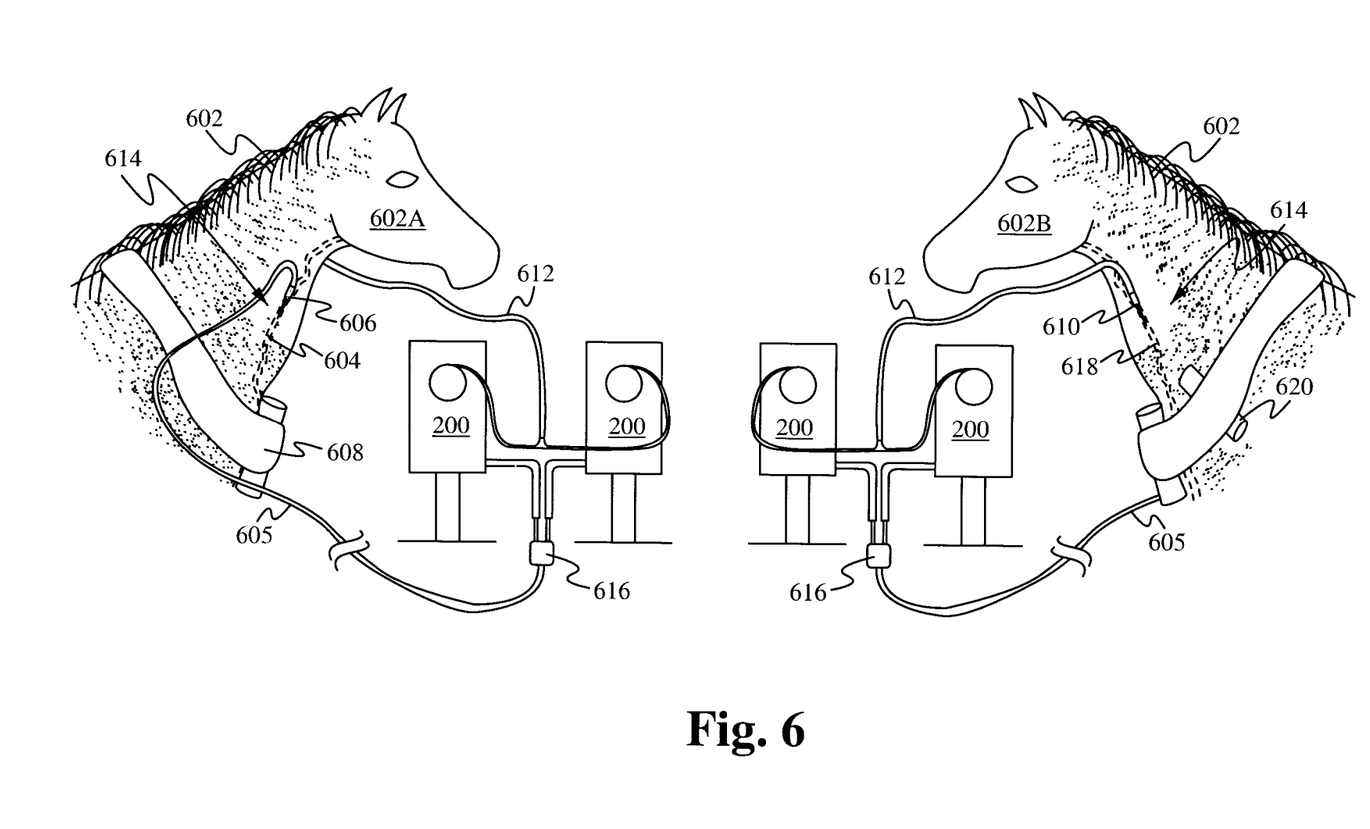
FIG. 6 illustrates a method of non-human plasmapheresis in accordance with some embodiments of the present application.

FIG. 6 illustrates the method of non-human plasmapheresis in accordance with some embodiments of the present application. The tubing lines are attached to the donor animal's 602 catheters via luer connections. In some embodiments, the tubing lines are EPS1 and EPS3 tubing lines. In some embodiments, EPS3 tubing line is connected to the near/right catheter 606 and EPS1 tubing line is connected to the far/left catheter 610. In some embodiments, both tubing lines are secured to the donor's neck with sutures. In some embodiments, the EPS3 is connected with the extraction catheter 606 located at the right side 602A of the donor animal 602. In some embodiments, the extraction catheter 606 inserts into the extraction vein 604 to receive blood from the donor animal 602. In some embodiments, an area 614 of the donor animal's hairs are removed to facilitate the insertion of the extraction catheter 606, 610. In some embodiments, the catheter 606 connects with the EP3 tubing line 605, which transports the blood received from the donor animal 602 to multiple plasmapheresis instrument 200 (FIG. 2) via a splitter 616. In some embodiments, the splitter 616 is able to split the blood received from a donor animal 602 into multiple plasmapheresis instruments 200 for concurrent processing. In alternative embodiments, the splitter 616 is able to combine the blood returned from the multiple plasmapheresis instruments 200 back to the donor animal 602 allowing the concurrent return of the blood from plural plasmapheresis instruments via one tubing and/or one catheter to eliminate the needs of inserting more than one catheter. The blood is able to be returned back to the donor animal 602 through the returning blood line 612, such as tubing line EP1. In some embodiments, the blood returning from the multiple plasmapheresis instruments 200 are combined at the splitter 616 and return through the return blood line 612 back to the vein 618 via the return catheter 610 at the left side 602B of the donor animal 602. The above described procedure is able to be performed in a continuous-flow manner. In some embodiments, the tourniquet 608 is used to occlude the extraction vein between the extraction catheter 606 and the heart of the donor animal (not shown) to facilitate the blood extraction. In some embodiments, the tourniquet 620 does not occlude the blood flow of the return vein 618 between the return catheter 610 and the donor animal's heart (not shown) to facilitate the blood return back to the donor animal 602.

V. Plasmapheresis: Continuous-Flow Operation

The modified equine plasmapheresis instruments 200 are advanced to simultaneously perform collection and reinfusion cycles. During this portion of plasmapheresis, equine plasma is harvested in the 20 liter bag and concentrated blood cells are returned to the donor. The following steps are performed:

(1) removing the three blue hemostats present on the tubing lines of the disposable set, using one hemostat to anchor the EPS1 and EPS3 lines next to the donor's tourniquet, storing the remaining two hemostats on the modified equine plasmapheresis instruments 200;

(2) pressing ∇ on both the modified equine plasmapheresis instruments 200 to initiate the priming sequence, allowing the instruments to perform a "BLOOD PRIME", a "BLD PRIME B" and a "FILTER PRIME," extracting whole blood during the priming sequence from the donor's catheter, mixing the blood with anticoagulant and using the mixed blood to prime the disposable set;

(3) allowing the instruments to collect and reinfuse following priming, allowing the blood flow and plasma flow to initially be 60 ml/min and 20 ml/min, respectively;

(4) allowing the instruments to automatically increase a blood flow rate to 150 ml/min;

(5) viewing one of three operating displays during continuous-flow operation. The displays are changed by pressing the F button. Press the F button one time to view blood flow, plasma flow, cuff pressure, venous pressure, transmembrane pressure and cycle number.

VI. Plasmapheresis: Donor Records and Donor Health

The donor is closely monitored throughout the plasmapheresis procedure. The modified equine plasmapheresis instruments 200 and Ohaus scale are also closely observed for proper operation. Donor health and equipment status is documented during plasmapheresis.

The procedure includes the following steps:

(1) returning to the donor's records and documenting the start time of plasmapheresis: the start time is when the ∇ buttons are pressed to begin the priming sequence;

(2) determining the donor's maximum allowable collection.

At the AUESPP, 22 ml of plasma is harvested for each kilogram of donor body weight. The specific gravity of plasma is approximately 1.035, which is used to convert volume into mass. The calculations are below:

Maximum Allowable Volume=Donor Weight kg×0.022 L/kg

Maximum Allowable Weight Maximum Allowable Volume L×1.035 kg/L;

(3) continuously monitoring the equine donor throughout the plasmapheresis procedure, paying attention to the donor's behavior, vital signs and catheter placement, evaluating donor pulse, respiratory rate, mucous membrane color and ECG and recording after harvesting approximately 10 L of plasma and at the end of the procedure;

(4) sedating the donor intravenously with Detomidine or Detomidine and Butorphanol during plasmapheresis under veterinary direction;

(5) documenting of unexpected events related to donor health and unexpected alert messages related to equipment on the records of plasmapheresis.

VII. Plasmapheresis: Ending Plasma Collection

Once plasmapheresis is complete, records are finalized, the plasma is processed, the donor receives IV (intravenous) fluids and equipment is cleaned.

The following steps are performed when applicable:

(1) Plasmapheresis is terminated under the following conditions:
 a) upon achieving the maximum allowable collection;
 b) donor's health is in jeopardy;
 c) the modified equine plasmapheresis instruments 200 fail to maintain plasma production;
 d) facility power loss; and
 e) project Director's request.

(2) The instruments are stopped by pressing the STOP button and the end time of plasmapheresis is documented.

(3) The weight and calculated volume of plasma harvested is recorded. Remaining paperwork is completed.

(4) EPS1, EPS3, AC and plasma lines are heat-sealed. The equine donor and plasma collection bag are separated from the disposable set. The disposable set is discarded in a labeled medical waste container.

(5) The 20L collection bag and plasmapheresis records are transported for further processing.

(6) The tourniquet is removed from the donor's neck and IV fluids are returned to the donor via gravity flow.

(7) Following fluid replacement, catheters and sutures are removed from the donor's neck.

(8) Excess blood is washed from the donor's body and the horse is released to its designated pasture.

Summary of the Continuous-Flow Operation

Figure 4:
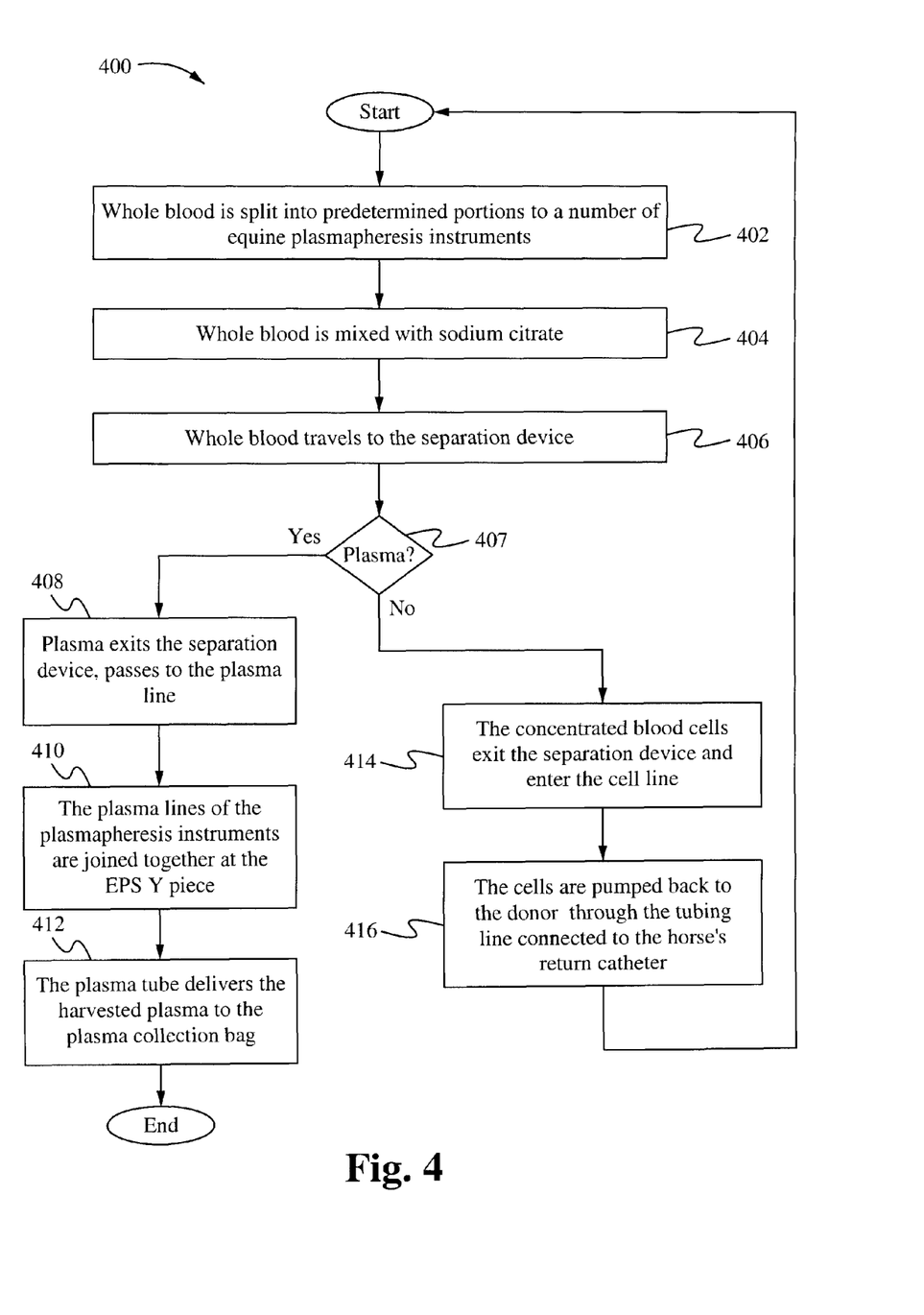
FIG. 4 shows a flow chart illustrating a method of using the equine plasmapheresis in accordance with some embodiments of the present application.

FIG. 4 illustrates the procedure of the continuous-flow operation. At the step 402, whole blood is removed from the donor horse via the EPS3 tubing line. The line divides and delivers blood to both donor lines of the modified Plasmacell-C sets and/or modified plasmapheresis instruments. A person skilled in the art would appreciate that a single modified Plasmacell-C set and/or a single modified plasmapheresis instrument are also able to be sufficient for the same purpose. At the step 404, whole blood enters the blood lines and is mixed with sodium citrate. The blood lines carry anticoagulated blood to each of the modified equine plasmapheresis instruments 200. At the step 406, whole blood travels past the air detector, through the blood pump and up to the separation device. The separation device acts as a rotating membrane filter to separate plasma from the cellular components of blood. At the step 407, the process goes to the step 408 if the substance is plasma and the process goes to the step 414 if the substance separated is not plasma, such as other blood cells. At the step 408, plasma exits the separation device, passes through a hemoglobin detector and continues down the plasma line. At the step 410, the two plasma lines join together at the EPS Y piece. At the step 412, the EPS2 delivers the harvested plasma to the EPS-20L collection bag. At the step 414, the concentrated blood cells exit the separation device and enter the cell line. At the step 416, the cells are pumped back to the donor through the EPS1 tubing line which is connected to the horse's return catheter.

The steps described above are examples in accordance with the embodiments of the present application. All the steps are optional and additional steps are able to be added. The orders of the steps are able to be performed in any sequences.

The equine plasmapheresis is used as examples in accordance with some embodiments of the present application. The present application is applicable to other animals, including but not limited to animals in the order of Perissodactyla, including animals belonging to the family of equidae. For example, horses, donkeys, and zebras.

The term modified Plasmacell-C set 300 are used interchangeable with the term disposable set 300, which are the tubing sets for transport of equine blood, throughout this disclosure. Further the term modified equine Autopheresis 200 is used interchangeably with the term modified equine plasmapheresis 200 throughout this disclosure.

In operation, some embodiments use a specifically designed plasmapheresis device for non-human animals. In some embodiments, the plasmapheresis device is designed for large animals, such as horse, donkey, and zebra. The plasmapheresis devices disclosed in the present application are able to be modified from plasmapheresis devices designed for human use. The embodiments of the present application provide the novel methods, systems, connections, and devices allowing the concurrent use of multiple plasmapheresis devices on one donor animal. The concurrent use of multiple plasmapheresis devices on one donor animal provides the benefits of reducing at least half of the time required to filter the same amount of blood and/or collect the same amount of plasma from one donor animal. Accordingly, the concurrent use of multiple plasmapheresis devices on one donor animal is able to save a significant amount of time required than if a single human-use plasmapheresis device is used to process the large amount of blood and plasma that are able to be received from the large animals. As such, the concurrent use of multiple plasmapheresis devices on one donor animal also provides the possibility of herding a big group of animals, including large animals, and efficiently collecting plasma of the animals from one animal immediately following another.

Further in some embodiments, the modified plasmapheresis devices provide a direct channel for returning separated blood back to the donor animal by sealing the lines from the separator to the blood reservoir and directly returning the blood, after going through the separator, directly back to the donor animal. Accordingly, the modification provides a real continuous-flow plasmapheresis method and device, which eliminates unnecessary retention of the filtered blood in the reservoir.

Moreover in some embodiments, the modified plasmapheresis devices provide a no-saline plasmapheresis procedure and have sealed saline lines. The sealed saline line reduces or eliminates the possibility of having air or air bubbles slipping into the blood transmission lines.

The plasmapheresis device of the present application provides advantages of high-speed, high volume, continuous-flow process of automated equine plasmapheresis procedures and instruments. The procedures and instruments are able to be applied and utilized in obtaining and collecting plasma from non-human animals.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A system for collecting non-human plasma comprising:
a. at least two non-human blood receiving devices; and
b. at least two non-human plasma separators coupled with the at least two non-human blood receiving devices, wherein the non-human plasma separators couple with a plasma collecting line and a blood returning line, and wherein the plasma collecting line receives non-human plasma while the blood returning line simultaneously returns blood cells back to the donor animal.

2. The system of claim 1, further comprising a donor blood line, wherein the donor blood line receives blood from a donor animal.

3. The system of claim 2, wherein a tourniquet is wrapped around the neck of the donor animal, partially occluding an extraction vein but not obstructing the return vein, in order to provide adequate blood flow during a plasmapheresis procedure.

4. The system of claim 2, wherein the donor blood line connects to a splitter, wherein the splitter splits the blood received from the donor animal into a first portion and a second portion.

5. The system of claim 4, wherein the first portion of the blood received is transferred to a first non-human blood receiving device and the second portion of the blood received is transferred to a second non-human blood receiving device.

6. The system of claim 5, wherein both the first and second non-human blood receiving devices contain an anticoagulation substance supplier for supplying an anticoagulation substance to prevent coagulation of the blood.

7. A system for collecting non-human plasma comprising:
a. at least two non-human blood receiving devices; and
b. at least two non-human plasma separators coupled with the at least two non-human blood receiving devices, wherein the non-human plasma separators couple with a plasma collecting line and a blood returning line, and wherein the plasma collecting line receives non-human plasma while the blood returning line simultaneously returns blood cells back to the donor animal, wherein the non-human plasma separators separate the non-human plasma from the non-human blood cells, wherein the separated non-human plasma from both the first non-human plasma separator and the second non-human plasma separator are combined and collected as one unit, wherein the separated non-human blood cells from the first non-human plasma separator are combined with the separated non-human blood cells from the second non-human plasma separator and returned to the donor animal through one catheter.

8. The system of claim 7, further comprising a donor blood line, wherein the donor blood line receives blood from a donor animal.

9. The system of claim 8, wherein a tourniquet is wrapped around the neck of the donor animal, partially occluding an extraction vein but not obstructing the return vein, in order to provide adequate blood flow during a plasmapheresis procedure.

10. The system of claim 8, wherein the donor blood line connects to a splitter, wherein the splitter splits the blood received from the donor animal into a first portion and a second portion.

11. The system of claim 10, wherein the first portion of the blood received is transferred to the first non-human blood receiving device and the second portion of the blood received is transferred to a second non-human blood receiving device.

12. The system of claim 11, wherein both the first and second non-human blood receiving devices contain an anticoagulation substance supplier for supplying an anticoagulation substance to prevent coagulation of the blood.

* * * * *